(12) United States Patent
Corace et al.

(10) Patent No.: US 10,603,278 B2
(45) Date of Patent: Mar. 31, 2020

(54) MICROSPHERES CONTAINING ANTHELMINTIC MACROCYCLIC LACTONES

(71) Applicant: FATRO S.P.A., Ozzano Dell'emilia (BO) (IT)

(72) Inventors: Giuseppe Corace, Ozzano Dell'emilia (IT); Eva Morbidelli, Ozzano Dell'emilia (IT); Laura Bertocchi, Ozzano Dell'emilia (IT); Lauretta Montecchi, Ozzano Dell'emilia (IT)

(73) Assignee: FATRO S.P.A., Ozzano Dell'Emilia (IT)

( * ) Notice: Subject to any disclaimer, the term of this patent is extended or adjusted under 35 U.S.C. 154(b) by 0 days.

(21) Appl. No.: 15/735,233

(22) PCT Filed: Sep. 6, 2016

(86) PCT No.: PCT/EP2016/070921
§ 371 (c)(1),
(2) Date: Dec. 11, 2017

(87) PCT Pub. No.: WO2017/045966
PCT Pub. Date: Mar. 23, 2017

(65) Prior Publication Data
US 2018/0177730 A1    Jun. 28, 2018

(30) Foreign Application Priority Data
Sep. 16, 2015   (IT) .................. 102015000052268

(51) Int. Cl.
| | | |
|---|---|---|
| A61K 9/16 | (2006.01) |
| A61K 9/00 | (2006.01) |
| A61K 31/365 | (2006.01) |
| A61K 9/14 | (2006.01) |
| A61P 33/10 | (2006.01) |
| A61K 31/7048 | (2006.01) |

(52) U.S. Cl.
CPC .......... *A61K 9/1617* (2013.01); *A61K 9/0019* (2013.01); *A61K 9/145* (2013.01); *A61K 31/365* (2013.01); *A61K 31/7048* (2013.01); *A61P 33/10* (2018.01)

(58) Field of Classification Search
CPC ...... A61K 9/1617; A61K 9/0019; A61P 33/10
See application file for complete search history.

(56) References Cited

U.S. PATENT DOCUMENTS

| 7,589,082 B2 * | 9/2009 | Savoir ................. A61K 9/0014 514/170 |
| 2004/0058896 A1 * | 3/2004 | Dietrich ............... A61K 9/1617 514/171 |

FOREIGN PATENT DOCUMENTS

| EP | 0525307 A1 | 2/1993 | |
| EP | 1197207 A2 | 4/2002 | |
| SK | 279867 B6 * | 4/1999 | .......... A61K 9/1617 |
| WO | 1999043304 A1 | 9/1999 | |

OTHER PUBLICATIONS

Saraf, A., "Preparation and evaluation of microspheres based long-acting depot injection using a novel biomaterial as a polymer", World J of Pharmacy and Pharmaceutical Sciences, vol. 3, Iss 10, 733-739.*
Search Report and Written Opinion of PCT/EP2016/070921 dated Dec. 6, 2016.

* cited by examiner

*Primary Examiner* — Gina C Justice
(74) *Attorney, Agent, or Firm* — Silvia Salvadori, P.C.; Silvia Salvadori

(57) ABSTRACT

Disclosed are microspheres containing 1% to 20% by weight of milbemycin, avermectin or a derivative thereof, 50% to 95% by weight of a fat, a wax or a mixture thereof, 0.1% to 10% by weight of a steroid lipid, preferably cholesterol, and 0.01% to 1% by weight of an antioxidant.

10 Claims, 3 Drawing Sheets

MICROSPHERES CONTAINING ANTHELMINTIC MACROCYCLIC LACTONES

This application is a U.S. national stage of PCT/EP2016/070921 filed on 6 Sep. 2016, which claims priority to and the benefit of Italian Application No. 102015000052268 filed on 16 Sep. 2015, the contents of which are incorporated herein by reference in their entireties.

The present invention relates to formulations in the form of injectable microspheres of macrocyclic lactones which are useful for the prevention and treatment of veterinary and human diseases.

PRIOR ART

Milbemycins and avermectins, which belong to the class of macrocyclic lactones (macrolides), are used for the prevention and treatment of diseases caused by nematodes and ectoparasites in animals and humans.

Moxidectin and milbemycin oxime are milbemycins, while examples of avermectins include ivermectin, eprinomectin and doramectin. Said products are administered orally, parenterally and topically (pour-on).

Parenteral formulations are preferred, because they enable a precise therapeutic dose to be administered on the basis of the animal weight.

The need for sustained-release parenteral formulations of milbemycins and avermectins is particularly felt in the veterinary profession.

In view of the lipophilic nature of said macrolides, solutions or suspensions with an oily or fatty base have mainly been proposed.

For example, WO2013137748 discloses parenteral formulations containing milbemycins or avermectins with mixtures of excipients such as oils, for example castor oil, and non-aqueous carriers, for example cyclic amides such as pyrrolidinones.

EP1136081 describes sustained-release formulations of macrocyclic lactones with a surfactant (sorbitan esters), a solvent and a co-solvent.

US20040241204 discloses an implant for subcutaneous administration based on mixtures of biodegradable silicones that release the macrocyclic lactone over a long period, namely about 4 weeks.

EP 525307 describes sustained-release parenteral microspheres containing fats, waxes and oil, preferably glyceryl stearate, fatty acids and antioxidants. An even more sustained action is disclosed in EP1197207, wherein the microspheres have a composition similar to those described in EP 525307, but do not contain the oily fraction.

EP 525307 discloses microspheres containing fat, preferably glyceryl stearate, triglyceride oil and an antioxidant, which release moxidectin for several weeks. EP1197207 discloses that the presence of glyceryl stearate alone further extends the release of moxidectin.

It has been demonstrated that the formulation described in EP1197207, currently marketed under the tradename of Guardian SR, has a half-life of 73 days in dogs.

DESCRIPTION OF THE INVENTION

The present invention relates to injectable microspheres containing macrocyclic lactones, in particular moxidectin, with a sustained therapeutic action similar to or greater than those of known formulations and the formulations currently on the market.

It has now surprisingly been found that if steroid lipids, preferably cholesterol, are used in the preparation of microspheres, sustained release of macrocyclic lactone is obtained. The microspheres according to the invention present the advantage, due to the presence of cholesterol, of stable release of moxidectin in the physiological temperature range of 36-40° C., thus guaranteeing uniform bioavailability characteristics in various animal species.

The use of cholesterol is also advantageous because it presents lower risks of toxicity than the ingredients used to date in the known formulations.

The endectocidal therapeutic efficacy lasts for over 6 months, which in practice means that a single annual administration to the animal is sufficient, as the life cycle of parasites, in particular nematodes, is about 6 months, and administration during the larval period inhibits and eliminates proliferation all year round. One annual administration is therefore sufficient for prevention and treatment against endo- and ectoparasites, which involves an obvious advantage in terms of therapeutic safety and the well-being of the animal.

DETAILED DESCRIPTION OF THE INVENTION

Figure 1:
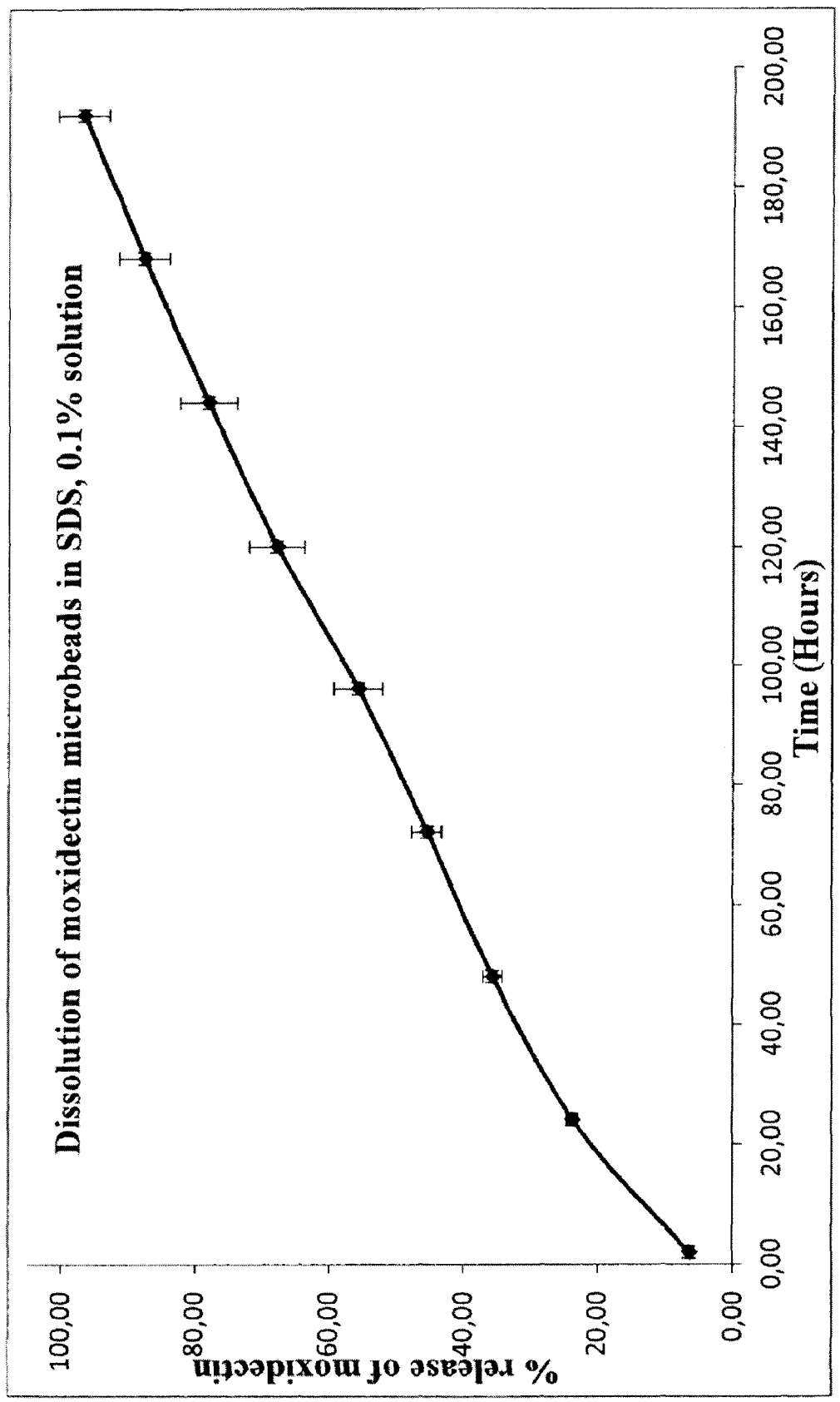
FIG. 1 shows the dissolution profile of the lipid microparticles in an 0.1% aqueous solution in SDS, n=12.

The microspheres according to the invention contain 1% to 20% by weight of milbemycin, avermectin or a derivative thereof, 50% to 95% by weight of a fat, a wax or a mixture thereof, 0.1% to 10% by weight of cholesterol, and 0.01% to 1% by weight of an antioxidant.

The preferred macrocyclic lactones belong to the milbemycin group. Particularly preferred compounds are described in EP 237339 and EP 259779, in particular moxidectin of the formula:

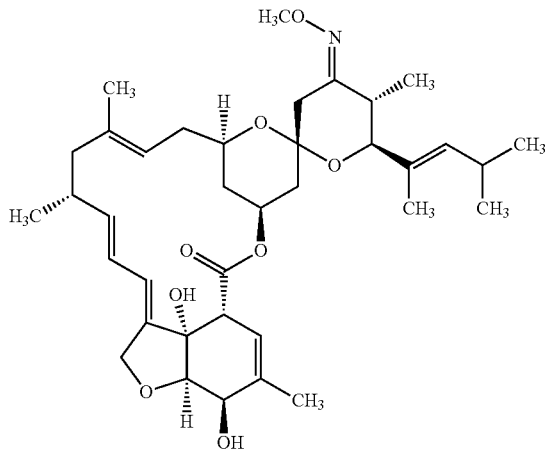 [SMILES: CO/N=C1\C[C@]2(C[C@@H]3C[C@@H](C/C=C(\C)C[C@@H](C)/C=C/C=C4\CO[C@@H]5[C@H](O)C(C)=C[C@@H](C(=O)O3)[C@]45O)O2)O[C@H](/C(C)=C/C(C)C)[C@H]1C]

Moxidectin is preferably present in percentages ranging from 1 to 15% by weight.

As avermectins have a Log P similar to that of moxidectin between 5.5 and 6.5, they can also be conveniently used as active ingredients in the formulations according to the invention. The term "fat" as used herein means glyceride esters of fatty acids, such as stearic and palmitic acid, preferably glyceryl stearate (GS), which are preferably present in percentages ranging from 60 to 90% by weight.

The term "wax" as used herein means saturated or unsaturated hydrocarbons, esters of long-chain fatty acids or mixtures thereof, generally with a melting point greater than 40° C.

The presence of cholesterol in quantities ranging from 0.1 to 10%, preferably from 0.1 to 5% by weight, gives moxidectin sustained-release characteristics which were wholly unexpected on the basis of prior knowledge.

The presence in the composition of glyceryl stearate and cholesterol microspheres gives moxidectin sustained-release characteristics similar or superior to those of the products currently on the market, and greater physicochemical stability of the microspheres.

It has also been found that cholesterol promotes general and local tolerability, especially at the injection site in the animal.

For parenteral administration, the microspheres are dispersed in a pharmaceutically and pharmacologically acceptable aqueous carrier.

The aqueous carrier can contain excipients in quantities ranging from 0.1 to 10% by weight. The excipients comprise cellulose derivatives, preferably hydroxypropyl methylcellulose (HPMC), ranging from 0.5 to 3%, preservatives from 0.1 to 0.5% and inorganic salts, such as NaCl, from 0.5 to 2% by weight.

Parenteral administration of said microspheres protects animals such as dogs, cats, cattle, sheep, pigs and horses against diseases caused by helminth, nematode, mite, endoparasite and ectoparasite infestations.

The microspheres according to the invention are prepared by dissolving the active ingredient in the mixture of excipients, fat, wax and lipid. The resulting hot solution is conveyed to a suitable sprayer, leading to the formation of microspheres of various dimensions, depending on the technical conditions used (spray-congealing).

Alternatively, the hot solution of active ingredient and excipients is cooled, and the resulting solid is ground in particular grinders to obtain microspheres.

The size of the microspheres is less than 800 μm, and they typically range from 20 to 300 microns, preferably from 90 to 200 μm.

The examples below describe the invention in greater detail.

EXAMPLE 1

Preparation of Microspheres Containing 10% Moxidectin and Cholesterol 861.9 g of glyceryl tristearate, 5 g of cholesterol, 12.5 g of hydrogenated palm oil and 15 g of carnauba wax were melted in a vessel fitted with magnetic stirring at 140° C. 105.6 g of moxidectin, purity 95%, containing 0.3-0.4% BHT, was added to the mixture of molten lipids. The resulting mixture was stirred at 140-150° C. until the active ingredient had solubilised. The solution obtained was nebulised in a cooling chamber using a pneumatic atomiser; when the resulting microdrops encountered a cold airstream they solidified and were collected with a cyclone system in the form of lipid microspheres. The microspheres produced were sieved to narrow the particle-size distribution. The particle-size fraction from 100 μm to 180 μm was divided between glass bottles in an inert atmosphere and sterilised with gamma rays.

EXAMPLE 2

Preparation of Microspheres Containing 10% Moxidectin and Ergosterol 861.9 g of glyceryl tristearate, 5 g of ergosterol, 12.5 g of hydrogenated palm oil and 15 g of carnauba wax were melted in a vessel fitted with magnetic stirring at 140° C. 105.6 g of moxidectin, purity 95%, containing 0.3-0.4% BHT, was added to the mixture of molten lipids. The resulting solution was atomised as described in example 1.

EXAMPLE 3

Preparation of Microspheres Containing 10% Moxidectin and Enriched with BHT 859.4 g of glyceryl tristearate, 5 g of cholesterol, 12.5 g of hydrogenated palm oil and 15 g of carnauba wax were melted in a vessel fitted with magnetic stirring at 140° C. 103.1 g of moxidectin, purity 97%, and 5 g of BHT, were added to the mixture of molten lipids. The resulting solution, containing 10% moxidectin and 0.5% BHT, was atomised as described in example 1.

EXAMPLE 4

Preparation of Reconstitution Liquid

The reconstitution liquid was prepared by solubilising 9 g of sodium chloride, 1.89 g of methyl paraben and 0.22 g of propyl paraben in 500 mL of water for injectables, heated to 75-80° C. 25 g of HPMC was added to the hot solution obtained, and the resulting dispersion was stirred for 10 minutes at 80° C. to promote swelling of the polymer. Finally, the remaining water was added until the volume of 1000 mL was reached. To promote complete solubilisation of the HPMC, the solution was stored overnight at 4° C. The pH of the solution was adjusted to 4.5-5.5 with 0.1N HCl. The reconstitution liquid was sterilised by filtration and divided between sterile bottles. The final composition of the reconstitution liquid is:

| | |
|---|---|
| NaCl | 0.900% |
| Methyl paraben | 0.189% |
| Propyl paraben | 0.022% |
| Hydroxypropyl methylcellulose (HPMC) | 2.500% |
| 0.1N HCl | q.s. to pH 4.5-5.5 |
| Water for injection | q.s. to 100 mL |

EXAMPLE 5

Dissolution of Microspheres

To evaluate the release kinetics of the active ingredient from the microspheres produced in example 1, a dissolution test was conducted using the following parameters:
Dissolving apparatus: Apparatus 2, blades
Dissolution medium: 0.1% aqueous solution of sodium lauryl sulphate.
Volume: 500 mL;
Temperature: 37° C.;

Stirring speed: 50 rpm;
Sampling: 2, 24, 48, 72, 96, 120, 144, 168 and 192 hours
Number of samples: 12

The results are set out in FIG. 1, which shows the dissolution profile of the lipid microparticles in an 0.1% aqueous solution in SDS, n=12.

As shown by FIG. 1, the active ingredient is released very slowly from the microspheres; less than 100% is released after 192 hours (8 days). The trend of the dissolution curve is particularly straight, which means that the active ingredient is released constantly over time with zero-order release kinetics.

EXAMPLE 6

Release of Moxidectin at Different Temperatures

It has been found that the addition of cholesterol makes the release of moxidectin less dependent on temperature variations.

In order to confirm the improved stability of formulations containing cholesterol, a comparative dissolution test was performed between the formulation of example 1 and the same formulation without cholesterol (see table below).

The test was conducted at different temperatures (36° C., 37° C., 38° C., 39° C. and 40° C.).

|  | (A) Formulation with cholesterol | (B) Formulation without cholesterol |
|---|---|---|
| Moxidectin | 10 | 10 |
| Glyceryl tristearate | 86.75 | 87.25 |
| Hydrogenated palm oil | 1.25 | 1.25 |
| Carnauba wax | 1.5 | 1.5 |
| Cholesterol | 0.5 | — |

The operating conditions of the dissolution test were as follows:

Dissolving apparatus: Apparatus 2, blades
Dissolution medium: 0.1% aqueous solution of sodium lauryl sulphate;
Volume: 500 mL;
Temperature: 36° C., 37° C., 38° C., 39° C. and 40° C.
Stirring speed: 50 rpm;
Sampling: 2, 24, 48, 72, 96, 120, 144, 168 and 192 hours
Number of samples: 12

Figure 2:
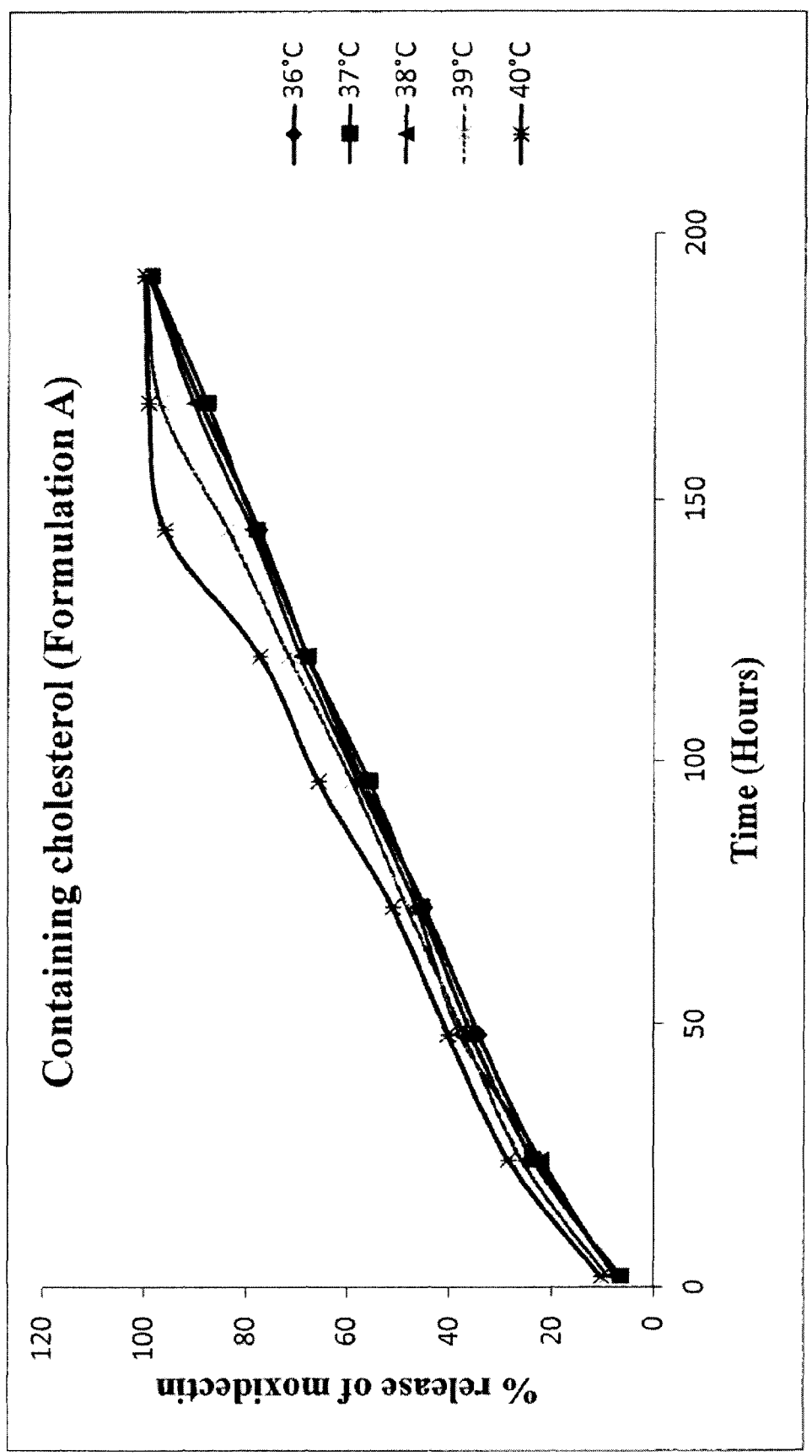
FIG. 2 shows the release profile of formulation A at different temperatures.
Figure 3:
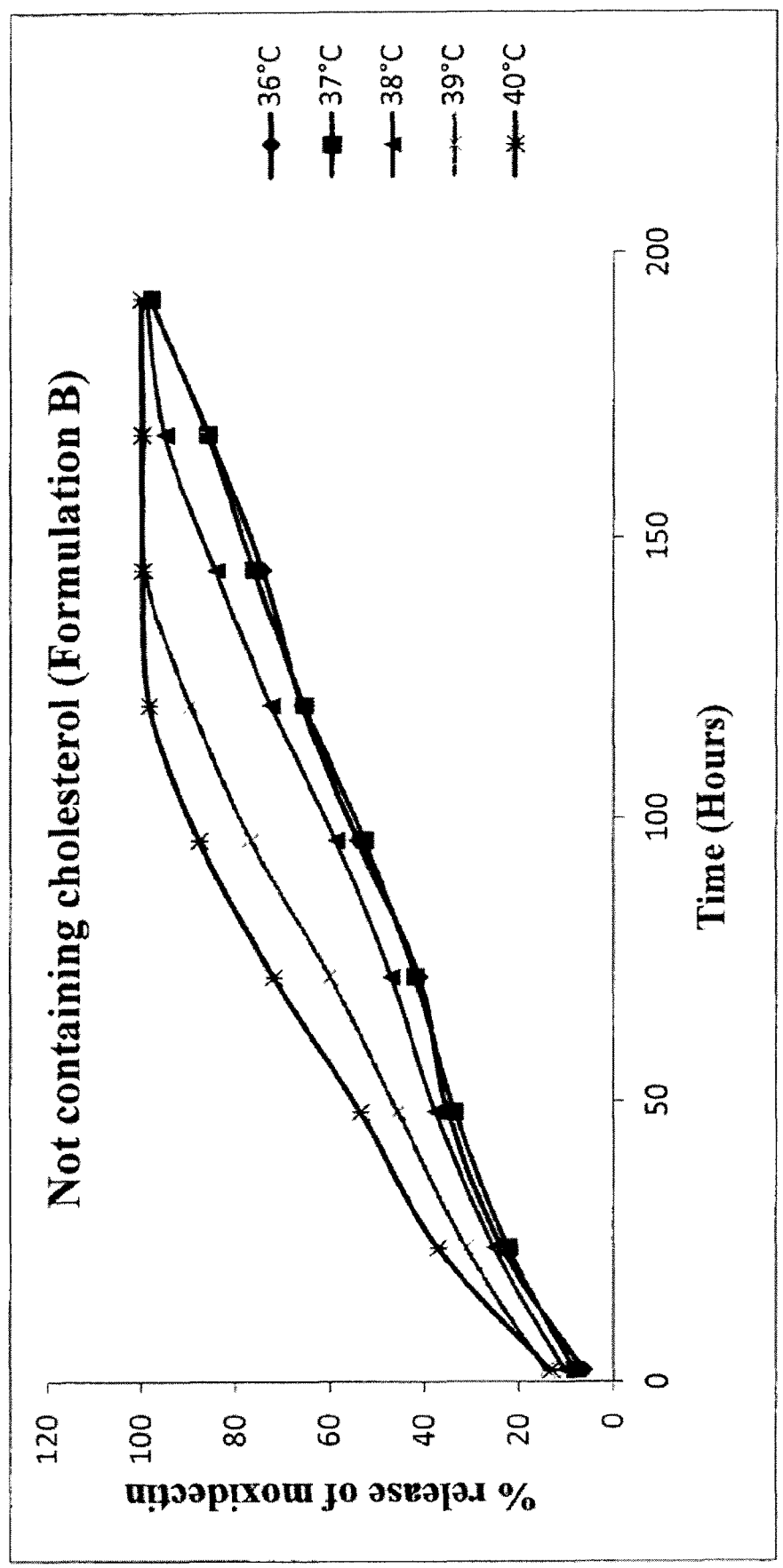
FIG. 3 shows the release profile of formulation B at different temperatures.

FIGS. 2 and 3 show the release profiles of formulations A and B at the different temperatures.

Comparison of FIGS. 2 and 3 shows that the formulation containing cholesterol is less susceptible to temperature variations than the formulation not containing it.

The stability of the formulations according to the invention is particularly important for use in animals with physiological temperatures ranging from 36 to 40° C.

The invention claimed is:

1. Microspheres containing 1 to 20% milbemycin, avermectin or a derivative thereof, 50% to 95% by weight of a fat or a wax or a mixture thereof, 0.1% to 10% by weight of cholesterol, and 0.01 to 1% by weight of an antioxidant, said microspheres being prepared by solubilizing said milbemycin, said avermectin or said derivative thereof, in said fat, said wax, or said mixture thereof.

2. Microspheres according to claim 1 wherein the milbemycin derivative is moxidectin, present in amounts ranging from 1 to 15%.

3. Microspheres according to claim 1 containing 60 to 90% by weight of a fat or wax or a mixture thereof.

4. Microspheres according to claims 1, wherein the fat or wax is a fatty acid ester.

5. Microspheres according to claim 4 wherein the fat is glyceryl tristearate.

6. Microspheres according to claim 1 wherein cholesterol is present in amounts ranging from 0.1 to 5% by weight.

7. Microspheres according to claim 1 containing 0.01 to 0.5% by weight of an antioxidant.

8. Microspheres according to claim 1 wherein the diameter of the microspheres is lower than 800 μm.

9. Pharmaceutical formulations for parenteral administration, comprising the microspheres of claim 1 and an aqueous carrier suitable for parenteral administration to animals.

10. Method of preventing or treating diseases due to helminths, nematodes and endo- or ecto- parasites in warm-blooded animals with the formulations of claim 9, said method comprising
   admininstering an effective amount of said formulations to said warm-blooded animals; and
   preventing or treating said diseases.

* * * * *